US008062880B2

(12) United States Patent
Freeman (10) Patent No.: US 8,062,880 B2
(45) Date of Patent: Nov. 22, 2011

(54) BIOMASS CULTIVATION SYSTEM AND CORRESPONDING METHOD OF OPERATION

(75) Inventor: Howard G. Freeman, Worcester, MA (US)

(73) Assignee: Freeman Energy Corporation, Topanga, CA (US)

( * ) Notice: Subject to any disclaimer, the term of this patent is extended or adjusted under 35 U.S.C. 154(b) by 693 days.

(21) Appl. No.: 12/049,468

(22) Filed: Mar. 17, 2008

(65) Prior Publication Data

US 2008/0254529 A1    Oct. 16, 2008

Related U.S. Application Data

(60) Provisional application No. 60/923,306, filed on Apr. 13, 2007.

(51) Int. Cl.
*C12M 1/00* (2006.01)
*C12N 1/12* (2006.01)
*C12N 1/20* (2006.01)

(52) U.S. Cl. ............... 435/257.1; 435/243; 435/289.1; 435/292.1

(58) Field of Classification Search ................ 435/243, 435/257.1, 289.1, 292.1
See application file for complete search history.

(56) References Cited

U.S. PATENT DOCUMENTS

| | | | |
|---|---|---|---|
| 2,854,792 A | 10/1958 | Juda | |
| RE24,822 E | 5/1960 | Pallotta et al. | |
| 3,131,131 A | 4/1964 | Wehner | |
| 3,218,758 A | 11/1965 | Konikoff | |
| 3,439,449 A | 4/1969 | Huff | |
| 3,879,266 A | 4/1975 | Sorensen | |
| 3,986,297 A | 10/1976 | Ichimura et al. | |
| 3,986,934 A | 10/1976 | Muller et al. | |
| 4,059,922 A | 11/1977 | DiGiacinto | |
| 4,127,233 A | 11/1978 | Maciaszek | |
| 4,165,834 A | 8/1979 | Pitchon et al. | |
| 4,209,943 A | 7/1980 | Moeller et al. | |
| 4,320,594 A | 3/1982 | Raymond | |
| 4,411,846 A | 10/1983 | Ulrich et al. | |
| 4,473,970 A | 10/1984 | Hills | |
| 4,594,965 A * | 6/1986 | Asher et al. ................ | 119/239 |
| 4,743,405 A | 5/1988 | Durao et al. | |
| 4,857,464 A | 8/1989 | Weathers et al. | |
| 4,952,511 A | 8/1990 | Radmer | |
| 4,954,257 A | 9/1990 | Vogelpohl et al. | |
| 4,970,166 A | 11/1990 | Mori et al. | |
| 4,994,391 A | 2/1991 | Hoffmann | |
| 5,054,688 A | 10/1991 | Grindley | |
| 5,137,828 A | 8/1992 | Robinson et al. | |
| 5,151,347 A | 9/1992 | Delente et al. | |
| 5,382,389 A | 1/1995 | Goodine et al. | |
| 5,534,417 A | 7/1996 | Arad et al. | |
| 5,714,379 A | 2/1998 | Phipps, Jr. | |
| 5,846,816 A | 12/1998 | Forth | |
| 5,848,752 A | 12/1998 | Kolacz et al. | |
| 5,981,271 A | 11/1999 | Doucha et al. | |
| 6,019,497 A | 2/2000 | Ingerttila et al. | |
| 6,069,004 A | 5/2000 | Teramachi et al. | |
| 6,156,561 A | 12/2000 | Kodo et al. | |
| 6,348,347 B1 | 2/2002 | Hirabayashi et al. | |
| 6,572,770 B1 * | 6/2003 | Stewart et al. ................ | 210/602 |
| 6,579,714 B1 | 6/2003 | Hirabayashi et al. | |
| 6,615,542 B2 | 9/2003 | Ware | |
| 6,667,171 B2 | 12/2003 | Bayless et al. | |
| 7,056,725 B1 | 6/2006 | Lu et al. | |
| 7,229,067 B2 | 6/2007 | Dimarzo et al. | |
| 2005/0118702 A1 | 6/2005 | Erhardt et al. | |
| 2005/0239182 A1 * | 10/2005 | Berzin ......................... | 435/166 |
| 2006/0273187 A1 * | 12/2006 | Morozov et al. ............. | 239/9 |
| 2007/0003442 A1 * | 1/2007 | Link et al. .................... | 422/99 |
| 2007/0125881 A1 | 6/2007 | Gansebom | |
| 2007/0231886 A1 | 10/2007 | Kahlert et al. | |
| 2007/0264708 A1 | 11/2007 | Bayless et al. | |
| 2007/0289206 A1 | 12/2007 | Kertz | |

FOREIGN PATENT DOCUMENTS

| | | |
|---|---|---|
| DE | 4006968 A1 | 9/1991 |
| FR | 2635531 A1 | 2/1990 |
| JP | 3-191775 | 8/1991 |
| JP | 9-251187 | 11/1991 |
| JP | 5-344879 | 12/1993 |
| JP | 6-133757 | 5/1994 |
| JP | 7-155168 | 6/1995 |
| JP | 8-322553 | 12/1996 |
| JP | 9-90739 | 4/1997 |
| SU | 969211 A1 | 10/1982 |
| SU | 1535572 A1 | 1/1990 |
| WO | WO-92/16486 A1 | 10/1992 |

OTHER PUBLICATIONS

International Search Report and Written Opinion for Application No. PCT/US08/03498, dated Jul. 21, 2008.
Barbosa, Maria J. et al., "Overhanging Shear Stress of Microalgae Cultures in Sparged Photobioreactors," *Biotechnology and Bioengineering*, vol. 85(1):78-85 (2004).
Berge, Stephen M. et al., "Pharmaceutical Salts," *Journal of Pharmaceutical Sciences*, vol. 66(1):1-19 (1977).
Levin, Gilbert V. et al., "Harvesting of Algae by Froth Flotation," *Appl. Microbiol.*, vol. 10(2):169-175 (1962).

* cited by examiner

*Primary Examiner* — Herbert J Lilling
(74) *Attorney, Agent, or Firm* — Morse, Barnes-Brown & Pendleton, P.C.

(57) ABSTRACT

A liquid culture medium containing photosynthetic organisms dispenses from a droplet generator combined with a screen in the presence of light, and in the presence of a gaseous medium to form a liquid culture medium gas-enriched with the gaseous medium. Specifically, the droplets exiting the droplet generator entrain the gaseous medium. The droplets and entrained gaseous medium then impinge upon a screen. As the droplets and entrained gaseous medium impinge upon the screen, the droplets splatter and change direction and velocity, thereby generating areas of high turbulence around the screen. This high turbulence results in additional and increased mixing of the gaseous medium to create a highly gas-enriched liquid culture medium which promotes improved growth rates and production of the photosynthetic organisms contained therein.

16 Claims, 5 Drawing Sheets

BIOMASS CULTIVATION SYSTEM AND CORRESPONDING METHOD OF OPERATION

RELATED APPLICATION

This application claims priority to, and the benefit of, co-pending U.S. Provisional Application 60/923,306, filed Apr. 13, 2007, for all subject matter common to both applications. The disclosure of said provisional application is hereby incorporated herein by reference in its entirety.

FIELD OF THE INVENTION

The present invention relates to a biomass cultivation system, and more particularly to a system capable of generating a gas-enriched liquid mixture containing a biomass in a suitable manner for cultivation of that biomass.

BACKGROUND OF THE INVENTION

It is well known that the photosynthesis of microorganisms such as algae consumes carbon dioxide (hereinafter "$CO_2$") and generates oxygen (hereinafter "$O_2$"). Algae are considered efficient converters of $CO_2$ and they have been cultivated using a variety of techniques. The primary nutrient requirements of algae are sunlight and carbon, $CO_2$ being the principal source of carbon. Other microorganisms may require other nutrients.

Biomass resulting from the photosynthesis of algae can be burned directly as fuel, or it can be processed further (e.g., dewatering, drying, etc.) to produce many other products of commercial and/or environmental value. For example, algae have been cultivated artificially for such diverse purposes as the cultivation of food (i.e., protein residues) for animals and humans; ingredients for cosmetics and human health foods; refined/fermented biofuels (e.g., biodiesel, ethanol, methanol, and the like); the treatment of sewage and waste waters; and the accumulation of radioactive wastes.

Various methods and equipment have been employed to culture algae. However, attempts to make the cultivation of microorganisms commercially viable have been limited by the amount of $CO_2$ that can be incorporated into the culture medium, the length of time the culture medium is exposed to light in the wavelength range that drives the light-dependent processes of photosynthesis (about 400 to about 700 nanometers ("nm")), and the degree to which light can penetrate the culture medium. Like many plants, algae are quite sensitive to the amount and type of light. Excessive light intensity can damage and kill algal cells. Insufficient light can result in low levels of photosynthesis and consequently reduced growth rates.

Perhaps the simplest procedures for cultivating algae have involved the use of shallow open ponds exposed to sunlight, whether man-made (hereinafter "raceway" ponds) or natural. Because sunlight can only penetrate the pond water to a limited depth, the raceway ponds are constructed to be relatively shallow to maximize the exposure of the algae to sunlight. Paddle wheels generate water turbulence, which increases the incorporation of $CO_2$ into the water, and circulates the algae back to the surface at a regular frequency, thereby increasing the exposure of the algae to sunlight. As a result, raceway ponds provide somewhat improved algae growth in comparison to natural ponds, but this form of algae cultivation is still considered insufficient for producing feedstock for commodity products.

Another approach has involved cultivating algae in wholly and/or partially covered trenches and ponds, optionally having electrically powered pumps and agitators. These configurations reduce the chances of contamination of the culture and permit more accurate control of temperature, respiration and other parameters. However, such configurations still fall short in providing adequate and uniform amounts of $CO_2$ and light to the algal cells.

Increased algal cultivation rates can be achieved in photobioreactors, which provide improved environmental control because they are not open to the atmosphere. However, algal cultivation in photobioreactors is still limited by $CO_2$ concentration and/or exposure to light. Thus, a consideration for modern photobioreactors involves providing a means for uniformly exposing the cells in the algal culture to the optimum amount of light and/or $CO_2$. Some of the efforts include varying the configuration of the photobioreactor chamber(s) (e.g., horizontal tubular chambers, vertical tubular chambers, "airlift" photobioreactors, various arrays of tubular chambers, and the like); improving the photomodulation of the algae in the culture medium; and providing turbulence in the liquid media to both incorporate more $CO_2$ and increase the frequency with which the algae contact light (e.g., by pumping and/or spraying the liquid media into the chamber in the presence of $CO_2$; by injecting $CO_2$ into the liquid media; by disposing the liquid media onto mechanical supports arranged spatially to minimize mutual shading; and the like).

In addition to the provision of a uniform and constant supply of light, cell culture density and the light path length through the culture medium can influence algal growth rates. As in conventional fermentation processes, it is usually desirable to obtain as high a rate of cell growth in as high a density of cell culture as possible, to maximize the amount of biomass produced per unit of time. Many of the same considerations apply to algal cultures as to bacterial cultures. For example, in addition to the light requirements, one must take into account the competition for nutrients, respiratory demands, viscosity and pumpability of the culture medium, and the like. However, an extremely high cell culture density results in cells more than a few millimeters from the light source being effectively shielded from the light. Also, as light travels through the liquid culture medium, it gets attenuated. Simply increasing the light intensity will not overcome these problems, because highly intense light can damage or kill cells.

To address these problems, particularly for industrial applications involving high-density microbial cultures that are amenable to continuous or large-scale batch recovery operations, photobioreactors have been designed that have closely spaced, large, transparent walls defining a light path and a fluid chamber within which the algal culture is contained. The transparent walls are illuminated with an appropriate light source to sustain the photosynthetic reactions of the cells. However, these configurations are relatively costly.

SUMMARY

There is a need for a biomass cultivation system providing sufficient algal growth inexpensively enough to enable cultivation of biomass for commodity products. The present invention is directed toward further solutions to address this need, in addition to having other desirable characteristics.

In accordance with one embodiment of the present invention, a biomass cultivation system includes a screened assembly configured to emit a gas-enriched discharge mixture during operation. A liquid culture medium containing at least one photosynthetic microorganism can be supplied to the screened assembly. A gaseous medium can be supplied to the screened assembly. A liquid culture medium reservoir can be positioned to receive the gas-enriched discharge mixture discharged from the screened assembly. The screened assembly can include a droplet generator with the liquid culture medium supplied thereto, the droplet generator having a discharge path along which emerging droplets travel, and a screen disposed to intersect the discharge path of the droplet generator. The emerging droplets in the discharge path can be exposed to the gaseous medium and the emerging droplets impinge upon the screen forming the gas-enriched discharge mixture.

In accordance with example aspects and embodiments of the present invention, the at least one photosynthetic microorganism includes an algal organism. The gaseous medium includes $CO_2$, air, or both. The liquid culture medium can be supplied by the liquid culture medium reservoir. A pump can be provided and configured to pump the liquid culture medium through the screened assembly. A light source can be positioned to illuminate the liquid culture medium, and/or the light source can be sunlight. The light source can supply light in a wavelength range of about 400 nm to about 700 nm to illuminate the liquid culture medium. The screen can include a wire mesh structure.

In accordance with further example aspects and embodiments of the present invention, the liquid culture medium can further include a surfactant in an amount sufficient to generate a foam gas-enriched mixture upon impinging on the screen. The surfactant can be, for example, vegetable oil or a derivative, shampoo, detergent, or any combination of some or all of these. A bioreactor can house the screened assembly, and/or the liquid culture medium reservoir, and/or a light source for illumination of the liquid culture medium. The liquid culture medium reservoir can be a natural pond, a raceway pond, a greenhouse reservoir, or a bioreactor reservoir.

In accordance with further example aspects and embodiments of the present invention, the system can be configured to pump the liquid culture medium through the screened assembly in periodic bursts.

In accordance with further example aspects and embodiments of the present invention, a method of cultivating a biomass using a biomass cultivation system is provided. The method can include providing the biomass cultivation system. A screened assembly can be configured to emit a gas-enriched discharge mixture during operation. A liquid culture medium can contain at least one photosynthetic microorganism supplied to the screened assembly. A gaseous medium can be supplied to the screened assembly. A liquid culture medium reservoir can be positioned to receive the gas-enriched discharge mixture discharged from the screened assembly. The screened assembly can include a droplet generator with the liquid culture medium supplied thereto, the droplet generator having a discharge path along which emerging droplets travel, and a screen disposed to intersect the discharge path of the droplet generator, wherein the emerging droplets in the discharge path are exposed to the gaseous medium and the emerging droplets impinge upon the screen forming the gas-enriched discharge mixture. The method can further include pumping the liquid culture medium through the screened assembly to generate the gas-enriched discharge mixture. The gas-enriched discharge mixture can be collected in the liquid culture medium reservoir.

In accordance with further example aspects and embodiments of the present invention, the at least one photosynthetic microorganism can include an algal organism. The gaseous medium can include $CO_2$, air, or both. The liquid culture medium can be supplied by the liquid culture medium reservoir. The liquid culture medium can be illuminated with a light source, for example in a wavelength range of about 400 nm to about 700 nm for algae. The gas-enriched discharge mixture discharged from the screened assembly can be illuminated. The screen can be a wire mesh structure. A surfactant can be added to the liquid culture medium in an amount sufficient to generate a foam gas-enriched mixture upon impinging on the screen, and can be, for example, vegetable oil or a derivative, shampoo, detergent, or any combination of some or all of these. The liquid culture medium reservoir can be a natural pond, a raceway pond, a greenhouse reservoir, or a bioreactor reservoir. The liquid culture medium can be pumped through the screened assembly in periodic bursts.

In accordance with further example aspects and embodiments of the present invention a method of biomass cultivation can include providing a liquid culture medium containing at least one photosynthetic microorganism and a surfactant. The liquid culture medium can be arranged into a plurality of cells having walls formed of the liquid culture medium and containing a gaseous medium therein. A predetermined intensity and wavelength range of light suitable as a nutrient to the photosynthetic microorganism can be provided. The plurality of cells can be substantially transparent to the light, and can support growth of the photosynthetic microorganism.

In accordance with further example aspects and embodiments of the present invention, the plurality of cells can be arranged to have a diameter of about 3 mm to about 30 mm. The walls of the plurality of cells can include a liquid culture medium volume fraction of about 4% to about 12% of a total volume of the plurality of cells.

BRIEF DESCRIPTION OF THE FIGURES

These and other characteristics of the present invention will be more fully understood by reference to the following detailed description in conjunction with the attached drawings, in which.

Other features and advantageous aspects of the disclosure will become apparent from the following detailed description of embodiments of the disclosure herein, which are provided as examples. It is to be understood that various features of the embodiments could be utilized independent of other features. In other words, not every feature of each embodiment need be incorporated in a given device or a manufacturing method in practicing the present disclosure. Thus, the illustrated embodiments are intended as examples and are not to be construed as limiting.

DETAILED DESCRIPTION

A particular problem not yet solved in the art of cultivation of photosynthetic organisms for use as fuel and other commodity products is the inability to economically provide sufficient amounts or concentrations of $CO_2$ and desired light to the organisms during the photosynthetic process. The present system and method of operation overcome this problem, thereby providing substantially increased growth rates for the photosynthetic organisms, including in relatively highly concentrated cell cultures, due to an improved approach for increasing gas levels available as a nutrient to biomass cultures while increasing exposure of the biomass cultures to light. Use of the inventive system and method substantially increase biomass yield per unit of time in comparison to other systems and methods in an economically efficient and feasible manner.

Illustrative embodiments of the present invention relate to a system providing improved methods of cultivating photosynthetic organisms. The system makes use of a liquid culture medium dispensed from a droplet generator combined with a screen in the presence of light, and in the presence of a gaseous medium (for most algae the gaseous medium is or includes $CO_2$), resulting in the formation of a liquid culture medium gas-enriched with the gaseous medium. Specifically, the motion and surface area of droplets exiting the droplet generator result in substantial entrainment of the gaseous medium. The droplets and entrained gaseous medium then impinge upon a screen shortly after emerging from the droplet generator. As the droplets and entrained gaseous medium impinge upon the screen, some of the droplets splatter and change direction and velocity, thereby generating areas of high turbulence around the wires of the screen. This high turbulence results in additional and increased mixing of the gaseous medium and droplet liquid culture mediums. As a result, the droplets flowing through the screen emerge as a gas-enriched discharge dispersing into the surrounding space. The dispersed droplets contain a concentration of gas that is substantially increased in comparison to the concentration of gas in the droplets prior to passing through the screen. The gas-enriched discharge can then be collected in a reservoir and re-supplied as the liquid culture medium in a continuous loop, which further increases the amount of $CO_2$ mixed into the medium and further increases exposure of the organisms in the dispersed droplets of the medium to light during cultivation.

The substantial mixing of gas (such as $CO_2$) and liquid culture medium (such as a medium containing algae) that occurs with the system and method of the present invention results in a substantial improvement over the mixing that can be achieved by prior attempts of spraying without the combined droplet generator and screen utilized in the present system, and promotes an unexpectedly high growth rate of the algae achievable in comparison with other known systems and methods.

FIGS. 1 through 7, wherein like parts are designated by like reference numerals throughout, illustrate examples embodiments of a system and method for biomass cultivation according to the present invention. Although the present invention will be described with reference to the example embodiments illustrated in the figures, it should be understood that many alternative forms can embody the present invention. One of ordinary skill in the art will additionally appreciate different ways to alter the parameters of the embodiments disclosed, such as the size, shape, or type of elements or materials, in a manner still in keeping with the spirit and scope of the present invention.

"Liquid culture medium", as utilized herein, refers to a liquid containing at least one photosynthetic microorganism that is capable of supporting reproduction of the at least one microorganism (hereinafter "liquid culture medium"). The photosynthetic microorganism can include a form of algae, or can be another form of microorganism, such that the present invention is not limited only to use with algal cultivation.

"Photosynthetic organism," as utilized herein and without alteration from its conventional meaning, refers to any organism capable of photosynthetic growth in a liquid culture medium, including but not limited to, algae. For the ease of explanation, "photosynthetic organism" will be referred to hereinafter as "algae" and/or "algal," depending on the context. Such a liquid culture medium can comprise, for example, water, algae, nutrients, and the like. However, the present invention is not limited to the exemplary use of algae as the photosynthetic organism, but can instead be utilized by other biomass organisms that could be cultivated in the environment provided by the system.

"Biomass", as utilized herein and without alteration from its conventional meaning, refers to the mass and/or accumulating mass of photosynthetic organisms resulting from the cultivation of such organisms using a variety of techniques. Various forms and species of micro- and macro algae include but are not limited to chlorella, spirulina and kelp, and are exemplary of biomass and are presently cultivated for some of these uses.

Figure 1:
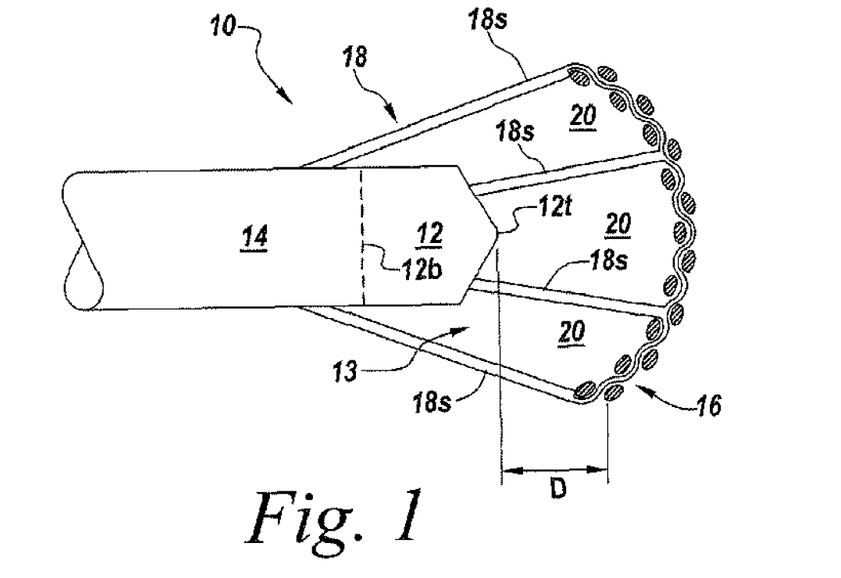
FIG. 1 is a cross-sectional schematic view of a screened assembly according to one embodiment of the present invention.

According to one embodiment of the present invention, and looking at FIG. 1, a screened assembly 10 for use in a biomass cultivation system is shown. In accordance with this particular example embodiment, the screened assembly 10 includes a droplet generator in the form of spray nozzle 12 that has a nozzle tip 12t and a base end 12b. The spray nozzle 12 is supported by, and fluidly connected to, a conduit 14 at the base end 12b. The conduit 14 is fluidly connected to a source of liquid culture medium, which can be a collection reservoir as later described, or can be another source. The screened assembly 10 also includes a screen 16 spaced apart, or distal, from the nozzle tip 12t by a distance "D," and supported on the conduit 14 by a screen support 18. Depending on various design and operating parameters of the spray nozzle 12, such as the angle and volume of discharge and the size of the droplets, distance D can be about 2 inches to about 6 or more inches. The screen 16 intersects with the droplets discharged from the spray nozzle 12. The screen 16 is formed of a mesh of woven wire having a selected spacing, pattern, and diameter. An exemplary suitable wire mesh has a spherical contour and a cross-sectional wire diameter of about 1/16 inch to about 1/8 inch, with about 2 to 6 wires per inch in a crisscross pattern. Those of ordinary skill in the art will recognize that the distance D, the contour of the mesh, the wire diameter, pattern, and spacing of the wires, can be varied as desired or needed to influence the properties and characteristics of the droplets emitted therefrom.

The screen support 18 includes a plurality of struts 18s extending from the conduit 14 to the screen 16 and defining a plurality of openings 20 disposed between the struts 18s. Although the screen support 18 is illustrated herein as a plurality of struts, it should be recognized that the screen support can be of any shape and/or configuration and can be supported by means other than the conduit 14, provided that the screen support includes openings for gas flow (e.g., openings 20) and provided it supports and maintains the screen 16 adjacent to and in spaced relation to the nozzle tip 12t. The spaced relation between the screen 16 and the nozzle tip 12t creates an open area 13 where a gaseous medium can be supplied. The gaseous medium can be supplied through an injection process, or through general exposure of the screened assembly 10 to an environment containing the gaseous medium, to intersect with the droplets. In the example embodiment discussed herein where the liquid culture medium contains an algal biomass, the use of $CO_2$ gas either supplied directly in a gaseous medium or as it naturally occurs in the air as the gaseous medium will suffice to fill the open area 13.

Figure 2:
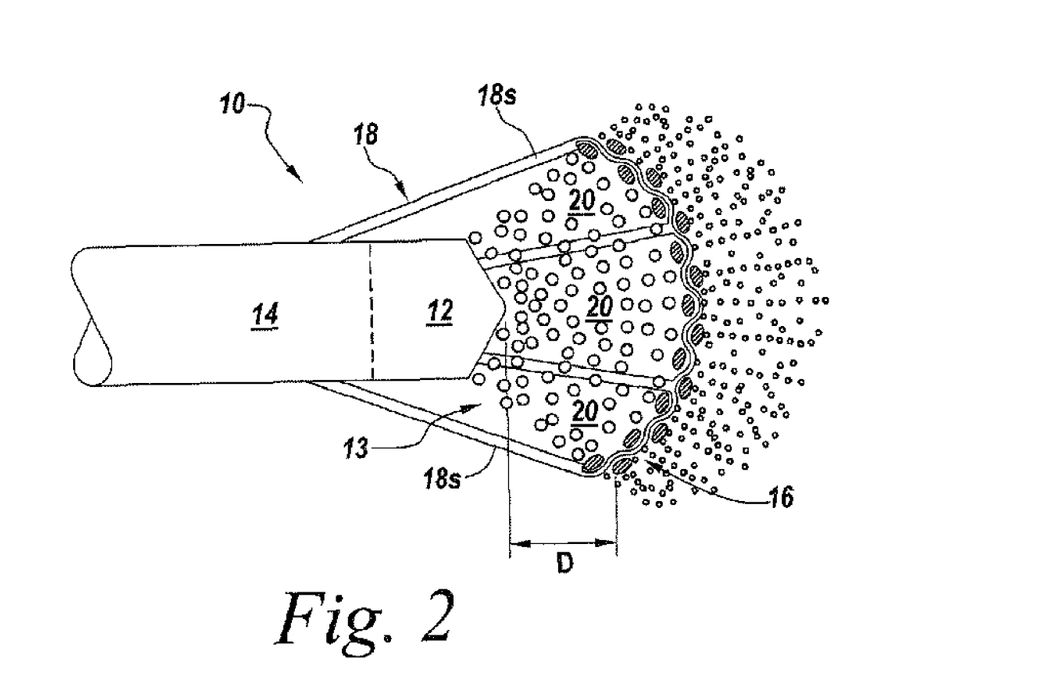
FIG. 2 illustrates operation of the screened assembly shown in FIG. 1.

In operation, as shown in FIG. 2, a liquid culture medium 11 is pumped into the conduit 14 and dispensed from the nozzle 12 into contact with a gaseous medium (such as a $CO_2$-containing gaseous medium), the liquid culture medium being converted in the nozzle into a plurality of droplets. The droplets then pass through the open area 13, intersecting with and entraining the gaseous medium therein, and impinge upon the screen 16, substantially mixing the entrained gaseous medium with the liquid culture medium droplets to form a gas-enriched discharge. If a surfactant is also provided, the action of the droplets impinging on the screen 16 forms a gas-enriched discharge of foam bubbles, containing the gas in the bubble walls and interiors.

Figure 3:
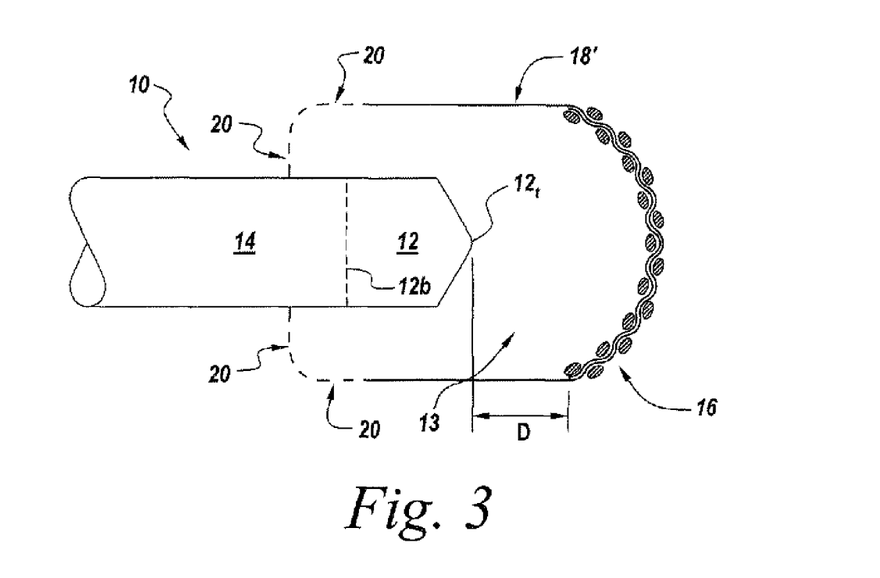
FIG. 3 is a cross-sectional schematic view of a screened assembly according to another embodiment of the present invention.

Another embodiment of a screened assembly 10' is shown in FIG. 3. The screened assembly 10' includes the droplet generator in the form of the spray nozzle 12 having the nozzle tip 12t and the base end 12b. The spray nozzle 12 is supported by and fluidly connected to the conduit 14 at the base end 12b. The conduit 14 is also fluidly connected to a source of liquid culture medium 15. The screened assembly 10' also includes the screen 16 spaced apart, or distal, from the nozzle tip 12t by a distance "D," and supported on the conduit 14 by a screen support 18'. Again, the open area 13 exists in this spaced apart area and includes the gaseous medium which intersects with the droplets from the spray nozzle 12. In the example embodiment, the screen support 18' is configured as a cage or tube that at least partially surrounds the spray nozzle 12 and serves to at least partially channel the entrained gaseous medium to the screen 16. Again, although configured in the present embodiment as a cage or tube, it should be recognized that the screen support 18' can take any shape and/or configuration and can be supported by means other than the conduit 14, provided that the screen support includes openings for gas flow (e.g., openings 20) and provided it supports and maintains the screen 16 adjacent to and in spaced relation to the nozzle tip 12t.

Figure 4:
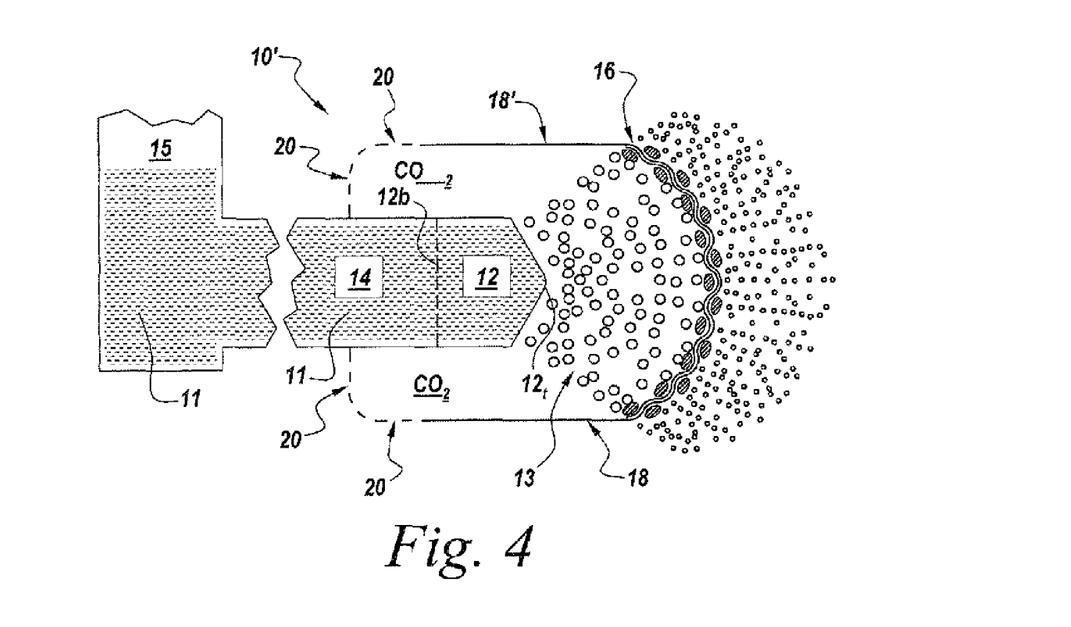
FIG. 4 illustrates operation of the screened assembly shown in FIG. 3.

As shown in FIG. 4, in operation, the liquid culture medium 11 is pumped into the conduit 14 and dispensed from the nozzle 12 into the open area 13 intersecting with the gaseous medium (such as a $CO_2$-containing gaseous medium in the case of most algae), forming a plurality of droplets from the liquid culture medium and entraining the gaseous medium therein. The droplets and entrained gaseous medium then impinge upon the screen 16, substantially mixing the gaseous medium and the liquid culture medium and forming a gas-enriched discharge. If a surfactant is also provided, the action of the droplets impinging on the screen 16 forms a gas-enriched discharge in the form of foam bubbles from the droplets, containing the gas in the bubble walls and interiors.

Figure 5:
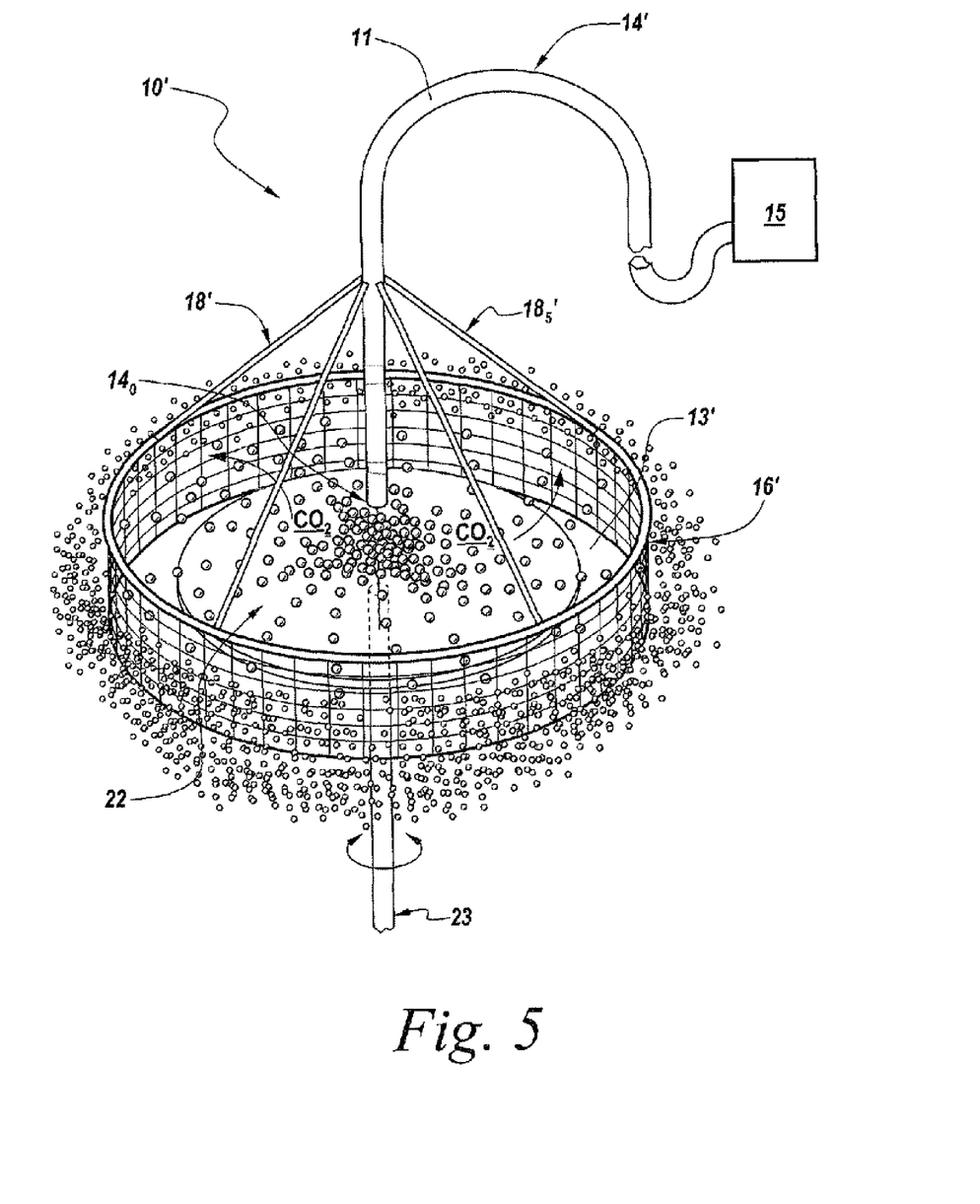
FIG. 5 is a cross-sectional schematic view of a screened assembly according to another embodiment of the present invention.

Another embodiment of a screened assembly 10" is shown in FIG. 5. As shown, the screened assembly 10" includes a droplet generator in the form of a spray disc 22 actuated by a motor and capable of spinning at high speeds (thousands of revolutions per minute ("RPM")), supported on a spindle 23. A screen 16' is disposed adjacent to disc 22 with an open area 13' existing inside the perimeter of the circular screen 16'. As shown, the screen 16' is in the shape of a band having a diameter approximately equal to that of the disc 22. The screen 16' is disposed coaxially around the disc 22, and is supported by a screen support 18" having struts 18s' attached to a conduit 14'. The conduit 14' has an outlet 14o and is fluidly connected to a source of liquid culture medium 15. It should be understood that the screen 16' can have a variety of shapes and be disposed anywhere adjacent to the disc 22, provided that a substantial amount of the droplets generated by the spinning action of the disc 22 impinge upon the screen 16'. For example, to intercept patterns of droplet dispersion of a disc 22 of a particular design, the screen 16' can have an approximately spherical contour and be disposed above the disc 22. The screen 16' can be supported by a variety of means. For example, the disc 22 can itself be the support for screen 16', in which case the screen spins with the disc 22. Alternatively, a support for the screen 16' can be a second disc disposed coaxially to and above disc 22 and attached to the conduit 14', having one or more openings for gas flow, and serving to at least partially channel the gaseous medium to the screen 16'.

In operation, the disc 22 is engaged to spin at thousands of RPM and the liquid culture medium is pumped into the conduit 14' and dispensed from the conduit outlet 14o onto the spinning disc 22 in the presence of a gaseous medium of the open area 13'. The rotation of the disc 22 causes a plurality of droplets to form from the liquid culture medium and disperse from the disc 22. The droplets entrain the gaseous medium and impinge upon the screen 16' resulting in substantial mixing of the gaseous medium and the droplet liquid culture medium and formation of a gas-enriched discharge. In the presence of surfactant, there results formation of a gas-enriched discharge in the form of foam bubbles from the droplets, containing the gas in the bubble walls and interiors. Those of ordinary skill in the art will recognize that a variety of spinning disc and other types of sprayers or droplet generators can be used in conjunction with the present screened assemblies and variations thereof to produce the gas-enriched discharge as described.

In the foregoing embodiments, the gaseous medium can be disposed in a closed, open, or partially closed chamber; or it can be an exhaust stream from manufacturing and/or energy production, channeled to flow adjacent to the nozzle, and the like. Alternatively, the gaseous medium can be air. Whether the gaseous medium is exhaust, air, or some other source, as previously stated herein it can contain $CO_2$, and will contain $CO_2$ if the biomass desired for cultivation is algae that require $CO_2$ as a nutrient for cultivation. Furthermore, if desired or necessary to achieve desired levels of gas entrainment, multiple sources of the gas can be provided by, for example, disposing another conduit supplying the gaseous medium adjacent to the droplet generator and/or the screen. In the case that the gaseous medium is exhaust from a manufacturing plant and contains $CO_2$, then the present invention can be utilized to absorb the $CO_2$ and remove it from the gaseous medium through its use as a nutrient for the cultivated algae.

The foregoing droplet generators found in the screened assemblies 10, 10', and 10" can be configured to produce a gas-enriched discharge in the form of a foam, such as the foam-generating nozzle described in U.S. Pat. No. 2,492,037 to Freeman et al, for example. Those of ordinary skill in the art will recognize that other types of foam-generating nozzles can also be used in the present methods to the extent they can mix the gaseous medium and the liquid culture medium approximately at a minimum as well as the droplet generators and screened assemblies described herein. However, it should be noted that simply spraying the liquid culture medium using a droplet generator into a chamber or bioreactor with $CO_2$ has been shown in its conventional arrangement to be insufficient to mix the $CO_2$ with the liquid culture medium to the degree necessary to promote the requisite rate of algae growth as provided herein. The addition of the screen portion of the screened assembly is instrumental in the case of the Freeman nozzle in thoroughly mixing the liquid culture medium and the gaseous medium to the extent required for the increased algal growth rates.

Each of the foregoing screened assemblies 10, 10', 10" are shown with one spray nozzle 12 or disc 22 and one screen 16, 16', but it should be understood that the screened assemblies are not limited to the use of one droplet generator per screen, or one screen per droplet generator. Rather, it should be understood that in the present system and method, a plurality of droplet generators can be used with one screen, and a plurality of screens can be used in series with one droplet generator. For example, the screened assemblies can have a screen of sufficient size such that a plurality of droplet generators can be disposed in adjacent, spaced apart relation thereto.

The foregoing screened assemblies 10, 10', 10" can be used in a variety of systems and/or apparatus such as, for example, with a liquid culture medium reservoir formed of natural or raceway ponds, and in greenhouses, bioreactors, and the like. In addition, a plurality of screened assemblies 10, 10', 10" and/or combinations of screened assemblies 10, 10', 10" can be used in the foregoing systems and/or apparatus. The screened assemblies can be arranged in a variety of configurations to optimize algal growth according to the particular apparatus and/or conditions. For example, algal growth can be increased in photobioreactors using one or more of the foregoing screened assemblies.

Figure 6:
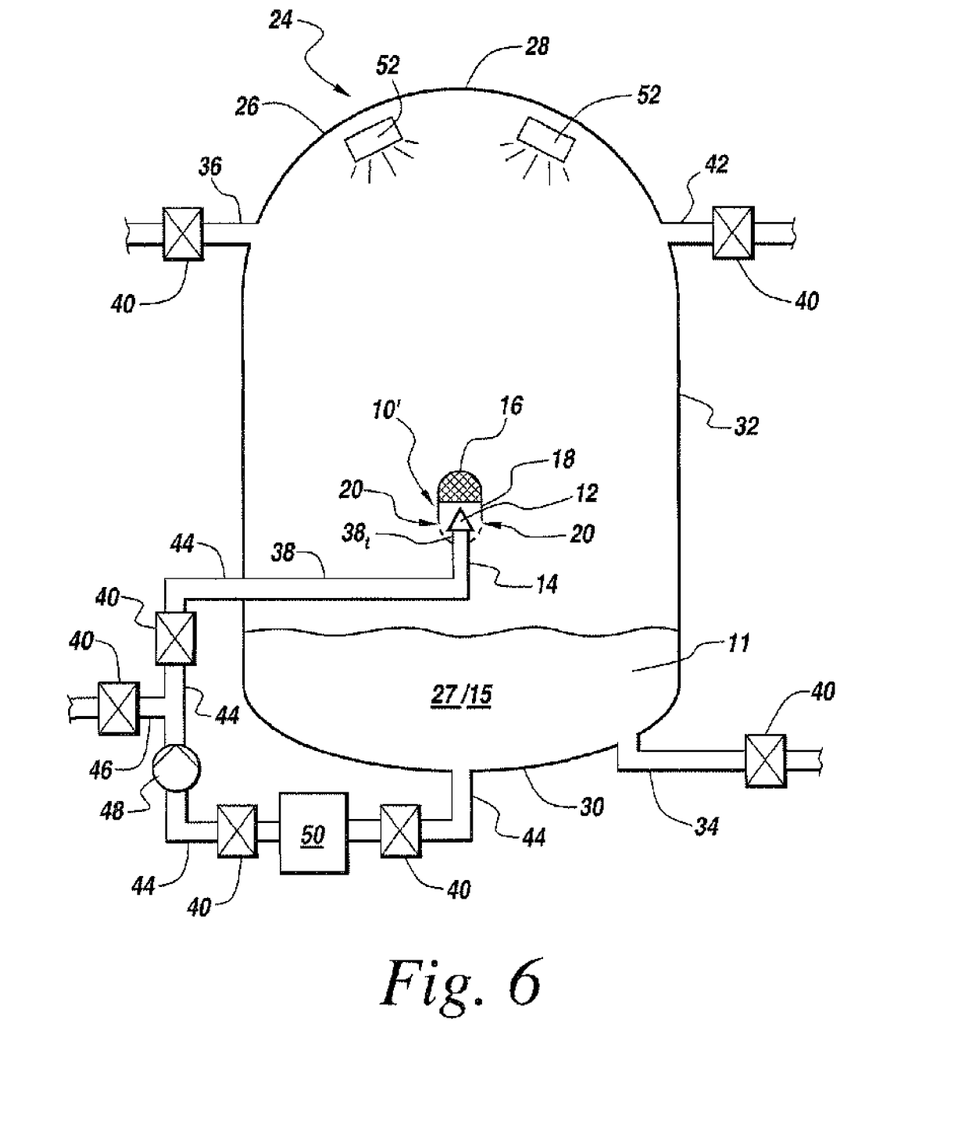
FIG. 6 is a cross-sectional schematic view of a photobioreactor according to one aspect of the present invention, including the screened assembly shown in FIG. 3.

FIG. 6 shows an exemplary photobioreactor in the form of bioreactor 24, which is one form of a biomass cultivation system, in accordance with one embodiment of the present invention. As shown, the bioreactor 24 includes a chamber 26 having an upper end 28, a lower end 30, and a substantially cylindrical sidewall 32 defining a reservoir region 27 at the lower end 30. The chamber 26 is illustrated herein as being substantially cylindrical, but it should be recognized that numerous shapes, sizes and/or configurations can be used, and that combinations of the same or different chambers can be used in series and/or in parallel. The chamber 26 can be made from a material that is capable of containing a liquid culture medium in the reservoir region 27 and capable of withstanding the process conditions used in the bioreactor. Optionally, the chamber 26 or a portion thereof can be formed from a material that is capable of transmitting light in the photoactive wavelength range into the chamber in order to drive photosynthesis of the algae or other biomass therein, such as, for example, glass, polymeric materials, composite materials, and the like. Suitable polymeric materials include, but are not limited to, polyethylene, polystyrene, polycarbonate, and the like. In addition, light in the photoactive wavelength range can be provided from a source other than sunlight, for example, one or more incandescent and/or fluorescent light bulbs or other light sources 52. Such light sources 52 can be disposed in the chamber 26 and/or external to chamber 26 (if the chamber is constructed of material that transmits light in the photoactive wavelength range). If the chamber 26 is constructed of a material other than one that transmits light in the photoactive range, then such light bulbs can be disposed in the interior of the chamber 26.

The bioreactor 24 includes various conduits fluidly connected to the chamber 26 for introducing raw materials into, for discharging processed materials from, and/or for re-circulating processed materials through the chamber 26, as desired or necessary. Those of skill in the art will recognize that the number, placement and shape of the conduits can vary, and that the conduits can be unitary, integral pieces, or alternatively a plurality of interconnecting unitary, integral pieces. When desired or necessary, valves 40 can be operatively connected to each of the various conduits to regulate the flow of material in and out of the chamber, or back into the chamber for further enrichment with $CO_2$. The valves 40 disclosed herein can be manual or automatic.

In the present embodiment, a first inlet conduit 34 is disposed at the lower end 30, and is adapted to introduce various raw materials (e.g., water, nutrients, algae, optional surfactant, and the like) into the reservoir region 27 as necessary or desired. It should be recognized that other raw materials can be used, and the selection and optimization of such materials can be determined by those of ordinary skill in the art using no more than routine experimentation. A second inlet conduit 36 is disposed adjacent to the upper end 28, and is adapted to introduce a gaseous medium into the chamber 26 (for example, a $CO_2$-containing exhaust stream from a power plant, air, and the like). A vent conduit 42 is disposed at or adjacent to upper end 28, and is adapted to discharge the gaseous medium from the chamber 26 as needed or desired to regulate the composition and/or pressure of the gaseous medium in the chamber.

At the reservoir region 27, a discharge conduit 44 is fluidly connected to the chamber 26 and to a re-circulating conduit 38, which is disposed in the sidewall 32 above the level of the reservoir region 27, and which extends at least partially into the chamber 26. As shown, the discharge conduit 44 is disposed at the bottom of reservoir region 27, but it should be understood that discharge conduit 44 can be disposed in multiple locations in the reservoir region 27, and in particular it can extend into the reservoir region 27 to provide discharge of liquid culture medium adjacent to the surface of the reservoir region 27. The re-circulating conduit 38 is adapted to receive the liquid culture medium from the chamber 26 via the discharge conduit 44 for re-circulation and further enrichment with gas, such as $CO_2$. A recovery conduit 46 is fluidly connected to the discharge conduit 44 between a pump 48 and the chamber 26, which is adapted to discharge the liquid culture medium for further processing to produce commercial products. The pump 48 is operatively connected to the discharge conduit 44 to pump the liquid culture medium through the discharge conduit 44 and into the recovery conduit 46, or into the chamber 26 for re-circulation and further enrichment with the gas, such as $CO_2$. The valves 40 can be operatively connected to the conduits 44, 46 to regulate the flow of liquid culture medium from the chamber 26 and into the recovery conduit 46, or back into the chamber 26.

The foregoing conduits can be made from one or more materials that are capable of containing a liquid culture medium, capable of withstanding the process conditions used in the bioreactor, and optionally capable of transmitting light. Suitable materials for the conduits include the same materials discussed above with respect to the chamber 26. The various conduits are illustrated herein as substantially tubular, and having a circular cross-section, but it should be understood that multiple shapes, sizes and/or configurations can be used. If desired or necessary, the conduits or any portion thereof can be constructed of materials that do not transmit light in the photoactive range, to accommodate the light-independent reactions of photosynthesis (also sometimes referred to as "dark reactions"). If desired, a strainer system 50 can be operatively connected to the discharge conduit 44 between the chamber 26 and the pump 48, in order to strain the liquid culture medium flowing through the discharge conduit 44.

In accordance with one example embodiment of the bioreactor 24, disposed at the terminal end 38*t* of the re-circulating conduit 38 is the screened assembly 10' previously discussed and detailed. The screened assembly 10' is disposed substantially in the center and at the lower end 30 of the chamber 26.

However, it should be understood that the screened assembly 10' can be disposed anywhere in the chamber 26, provided that when in operation the nozzle 12 is positioned above the level of the reservoir region 27. In addition, although only one screened assembly 10' is shown in the chamber 26, it should be understood that a plurality of screened assemblies 10, 10', 10" can be used in the present system and method, in multiple different operable configurations and/or combinations, and that the size and location of the screened assemblies 10, 10', 10" can vary. If desired or necessary, additional mechanical supports can be disposed in the chamber 26 for nozzle assemblies, interior lights, discs, screen, and the like.

Also if desired or necessary, a heater/heat exchanger (not illustrated) can be operatively connected to the chamber 26 for regulating the temperature of the bioreactor 24; a supplemental light source can be disposed in the interior or exterior of the chamber 26 in order to transmit light into the chamber 26 when sunlight is not available and/or during operation; a controller (not illustrated) can be operatively attached to the pump, automatic valves and heater; and a source of power (not illustrated) can be operatively connected to all of the foregoing in order to supply power for operating any automatic features of the bioreactor 24.

Figure 7:
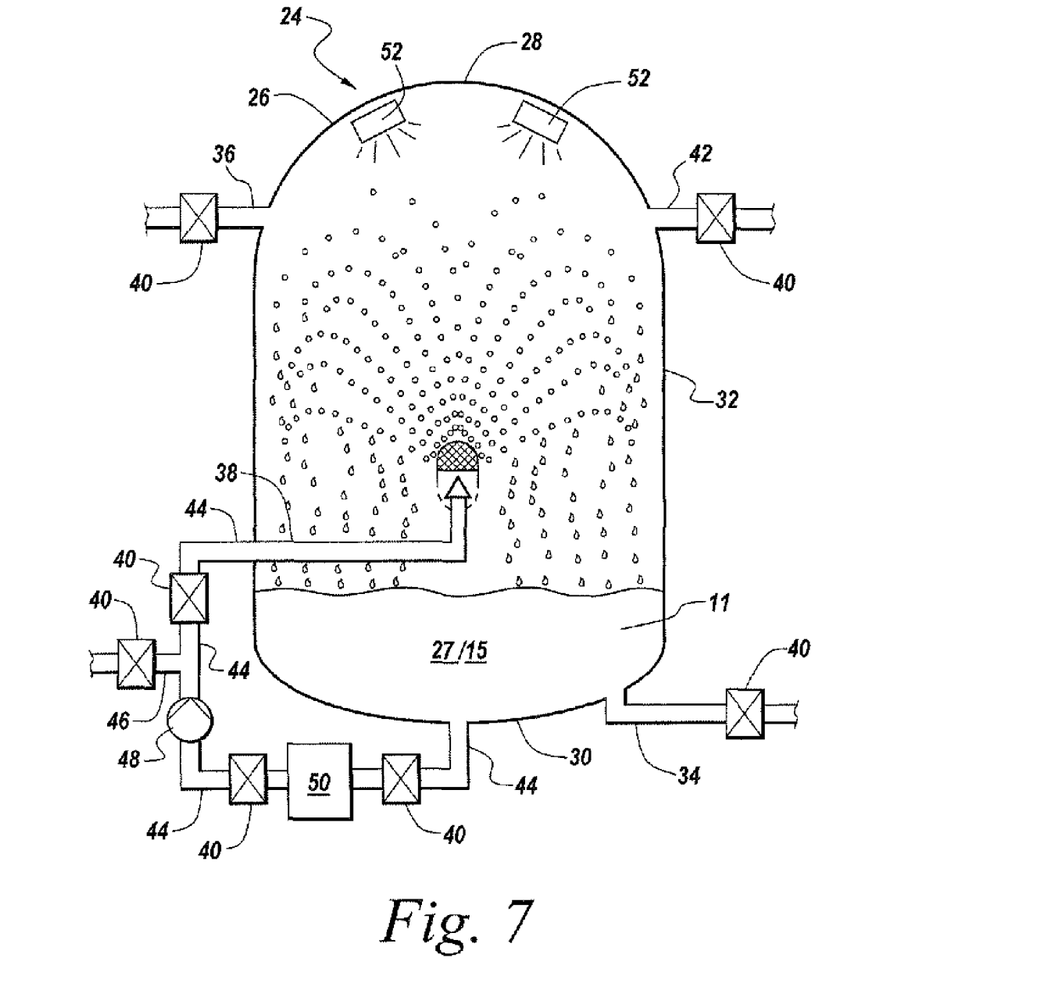
FIG. 7 illustrates operation of the photobioreactor shown in FIG. 6.

The operation of bioreactor 24 will now be explained with reference to FIGS. 6 and 7 and using the example of cultivating algae with the introduction of $CO_2$ gas and light. The bioreactor 24 can be operated on a continuous basis, or in batches. In operation, a sufficient amount of gaseous medium from an external source, such as the flue emissions from a coal-burning power plant and corresponding $CO_2$ contained therein, is introduced into the chamber 26 via the second inlet conduit 36. In an exemplar embodiment, the $CO_2$ concentration is about 2% to about 6%, by volume, at a pressure of approximately atmospheric pressure in the chamber. It should be understood that the pressure and concentration of $CO_2$ (or other desired gas) can be varied as desired or necessary, and that additional gases, including air, can be introduced via the second inlet conduit 36 if desired or necessary in order to maintain the desired gas composition and/or pressure in the chamber. Similarly, the vent conduit 42 can be used to discharge the gaseous medium from the chamber 26 as needed or desired to maintain the desired chamber pressure and gaseous medium composition. It should be understood that additional conduits can be fluidly connected to the chamber 26 in order to facilitate regulation of the gaseous and/or liquid culture medium in the chamber at desired and/or optimum conditions.

Various raw materials (e.g., water, algae, nutrients, optionally a surfactant, and the like) that make up the liquid culture medium are introduced into the reservoir region 27 via the first inlet conduit 34 until reaching a desired level below the level of the nozzle 12. Power to the system is turned on, activating the pump 48, and the liquid culture medium is then drawn into the discharge conduit 44 and into the chamber 26 via the re-circulating conduit 38.

The droplet generator, such as for example the spray nozzle 12, discharges the liquid culture medium as a plurality of droplets, and the droplets entrain the gaseous medium in the chamber (which includes gas such as for example $CO_2$), and impinge upon the screen 16 shortly thereafter. As illustrated in FIG. 7, the gas-enriched discharge disperses into the lighted chamber around the screened assembly 10'. As a result of the formation and dispersion of the droplets that occurs during this process, in the case of culturing algae, more algae in close proximity to $CO_2$ can receive sufficiently intense light for photosynthesis during the period of time from gas-enriched discharge emergence until the discharged liquid medium falls back and dissolves into the liquid culture medium in the reservoir region 27. This is primarily because of a reduction in attenuation of the light due to the scattering of the droplets, and because of reduction of mutual shading by the algae due to the dispersion of the gas-enriched discharge in space. Also, this period of time can be lengthened, and the access of the algae to light and $CO_2$ can be enhanced, by incorporation of a surfactant or other foaming agent into the liquid culture medium. Depending on the chemical composition and concentration of the foaming agent, the particular design characteristics of the screened assembly, and the velocity of the gas-enriched discharge emerging from the spray nozzle (or emerging from the spray disc, in the case of such embodiments), the gas-enriched discharge can emerge from the screen in the form of a foam comprised of a plurality of substantially transparent "wet" bubbles. In accordance with one example implementation of the present invention, the bubbles comprise diameters in the range of about 3 millimeters (mm) to about 30 mm, with an average diameter of about 5 mm to about 10 mm. The walls of the bubbles comprise a liquid culture medium volume fraction of about 4% to about 12% of the total volume of the bubbles. The liquid culture medium that makes up the walls has substantially increased concentration of $CO_2$, and the interiors of the bubbles contain $CO_2$.

If desired or necessary, the liquid culture medium can be pumped to and discharged from the droplet generator in bursts (for example, about 20 to 120 seconds per burst) to conserve energy and to allow accumulation of a collection of foam of desirable thickness (for example, about 3 to 10 centimeters) on the surface of the liquid culture medium in reservoir region 27. If desired or necessary, mechanical supports (not illustrated) for the foam can be disposed horizontally or at angles above the level of the liquid culture medium in reservoir region 27, on which the foam can accumulate and from which the foam can drain back into the liquid culture medium in reservoir region 27 over a desirable period of time (about 10 minutes to about 30 minutes). During the time the algae are suspended in the foam, they can continue to be in close proximity to the $CO_2$ present in the bubble walls and the interior of the bubbles. As the foam drains, algae in the successive layers of bubbles at the top of the remaining foam pile can continue to remain relatively un-shaded and to receive sufficiently intense light for photosynthesis. Additionally, the foam acts as a blanket, which reduces the escape of $CO_2$ from the liquid culture medium in the reservoir, thereby further increasing the duration of contact of $CO_2$ with algae. These are highly desirable outcomes of this process, are inexpensive to implement, and contributory to the substantial increase in the growth of the biomass.

More specifically when the liquid culture medium includes a surfactant, it can be an additive such as a liquid detergent, or can be a natural component of the algae, or both. In fact, examples of surfactants that can be utilized with algae include but are not limited to vegetable oil based surfactants, any biocompatible surfactant, and/or shampoos. The liquid culture medium with the surfactant is dispensed from the droplet generator in the presence of light, and in the presence of a gaseous medium (such as $CO_2$), forming a plurality of droplets of the liquid culture medium. The droplets entrain the gaseous medium and impinge upon a screen shortly thereafter, resulting in substantially increased mixing of the gaseous and droplet liquid culture mediums. Due to the presence of the surfactant, the gas-enriched discharge emerges from the screen in the form of foam bubbles, having walls made up of liquid culture medium having substantially increased concentration of $CO_2$ in comparison to the concentration of $CO_2$ in the droplets of liquid culture medium prior to impinging upon the screen, and also having hollow interiors containing the gaseous medium.

The foam bubbles have substantially larger volume than the droplets, effectively distributing the algae over a larger space, thereby further reducing the light shading of algae by other algae. The foam bubble walls are relatively thin, further reducing the average light path length through the liquid culture medium, thereby allowing the algae to receive light of higher intensity. The foam bubbles have a substantial surface area of liquid culture medium that can be contacted by the $CO_2$ present in both the exterior gaseous medium and the hollow interior of the foam bubbles, thereby allowing additional carbon transfer to the algae, beyond the amount available from the increased concentration of $CO_2$ within the foam bubble walls. Further, since the foam bubbles can be sustained in space for a substantially longer period of time than the non-foam gas-enriched discharge, substantially more light energy and $CO_2$ can be utilized by the algae in the foam bubble walls. These properties of the foam bubbles effectively allow the use of higher concentrations of algae in the liquid culture medium, which is highly desirable, while also promoting substantially increased carbon transfer and photosynthesis, resulting in substantially increased algal growth rates in relatively high cell culture densities, in comparison to other systems and methods. The bubbles can drain back into the liquid culture medium. The combination of higher algal concentration and higher algal growth rate contributes substantially to the increased biomass yield per unit of time that can be achieved in comparison to other systems and methods, and is relatively inexpensive in comparison thereto.

The gas-enriched discharge and/or bubbles eventually fall back/drain and dissolve into the reservoir, and the process is repeated until the liquid culture medium in the reservoir is sufficiently enriched with algae for harvesting, at which point the liquid culture medium in the reservoir, or a portion thereof, is removed from the chamber via the discharge conduit 44 and the recovery conduit 46. The reservoir region 27 can then be replenished with fresh raw materials via the first inlet conduit 34. Also, the screened assemblies can be used in a variety of cultivation systems and/or apparatus in addition to a photobioreactor. For example, the screened assemblies can be used in natural ponds, raceway ponds, greenhouses, and the like, whether wholly or partially covered, or uncovered. To do so, a conduit can be disposed that supplies liquid culture medium (and/or the raw materials to form the liquid culture medium) to the pond, to a reservoir or sump in a greenhouse, etc., effectively allowing the pond, greenhouse reservoir or sump, etc. to serve as the reservoir region 27. If desired or necessary, various pumps, agitators, and the like can be disposed in these cultivation systems, as would be understood by one of ordinary skill in the art. One or more $CO_2$-containing gaseous streams (e.g., air, flue gas from power plant, and the like) can be provided adjacent to the screened assemblies so that during operation, the $CO_2$ can be entrained and mixed in the liquid culture medium. Also, the screened assemblies can be used to initially increase the concentration of $CO_2$ in water rather than in liquid culture medium, with or without the addition of a surfactant, not necessarily in the presence of light, for subsequent use of the $CO_2$-enriched water, in bulk form or in the form of gas-enriched discharge or foam, to supply $CO_2$ to photosynthetic microorganisms and more generally plants, for the purpose of enhancing growth. For example, in an environment in which algae are growing at the surface of a pond, a conduit can be disposed that, via a pump, supplies water from beneath the surface of the pond to a screened assembly disposed above the algae, which mixes the water with supplied $CO_2$ and sprays the mixture onto the algae.

The system(s) and method(s) of the present invention disclosure can provide a more economical source of biofuels, a more economical source of oil that can be refined into biodiesel, and a more economical source of biomass that can be converted to ethanol. The biomass generated by the system(s) and method(s) of the present invention can be combusted directly or used to manufacture food or other useful products, mitigation of pollutants from power and processing plants, generation of oxygen, and the like, depending upon its particular implementation.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the present invention, and exclusive use of all modifications that come within the scope of the appended claims is reserved. It is intended that the present invention be limited only to the extent required by the appended claims and the applicable rules of law.

It is also to be understood that the following claims are to cover all generic and specific features of the invention described herein, and all statements of the scope of the invention which, as a matter of language, might be said to fall therebetween.

What is claimed is:

1. A biomass cultivation system, comprising:
    a screened assembly configured to emit a gas-enriched discharge mixture during operation;
    a liquid culture medium containing at least one photosynthetic microorganism supplied to the screened assembly;
    a gaseous medium supplied to the screened assembly; and
    a liquid culture medium reservoir positioned to receive the gas-enriched discharge mixture discharged from the screened assembly;
    wherein the screened assembly comprises:
        a droplet generator with the liquid culture medium supplied thereto, the droplet generator having a discharge path along which emerging droplets travel; and
        a screen disposed to intersect the discharge path of the droplet generator;
        wherein the emerging droplets in the discharge path are exposed to the gaseous medium and the emerging droplets impinge upon the screen forming the gas-enriched discharge mixture.

2. The biomass cultivation system of claim 1, wherein the at least one photosynthetic microorganism comprises an algal organism.

3. The biomass cultivation system of claim 1, wherein the gaseous medium comprises $CO_2$, air, or both.

4. The biomass cultivation system of claim 1, wherein the liquid culture medium is supplied by the liquid culture medium reservoir.

5. The biomass cultivation system of claim 1, further comprising a pump configured to pump the liquid culture medium through the screened assembly.

6. The biomass cultivation system of claim 1, further comprising a light source positioned to illuminate the liquid culture medium.

7. The biomass cultivation system of claim 1, wherein a light source supplies light in a wavelength range of about 400 nm to about 700 nm to illuminate the liquid culture medium.

8. The biomass cultivation system of claim 1, wherein the gas-enriched discharge mixture discharged from the screened assembly is illuminated by sunlight, artificial light, or both.

9. The biomass cultivation system of claim 1, wherein the screen comprises a wire mesh structure.

10. The biomass cultivation system of claim 1, wherein the liquid culture medium further comprises a surfactant in an amount sufficient to generate a foam gas-enriched mixture upon impinging on the screen.

11. The biomass cultivation system of claim 1, wherein the liquid culture medium further comprises a surfactant in an amount sufficient to generate a foam gas-enriched mixture upon impinging on the screen, the surfactant comprising vegetable oil or a derivative, shampoo, detergent, or any combination thereof.

12. The biomass cultivation system of claim 1, further comprising a bioreactor housing the screened assembly.

13. The biomass cultivation system of claim 1, further comprising a bioreactor housing the screened assembly, wherein the bioreactor further houses the liquid culture medium reservoir.

14. The biomass cultivation system of claim 1, further comprising a bioreactor housing the screened assembly, wherein the bioreactor further houses a light source for illumination of the liquid culture medium.

15. The biomass cultivation system of claim 1, wherein the liquid culture medium reservoir comprises a natural pond, a raceway pond, a greenhouse reservoir, or a bioreactor reservoir.

16. The biomass cultivation system of claim 1, wherein the system is configured to pump the liquid culture medium through the screened assembly in periodic bursts.

* * * * *